(12) United States Patent
Voudouris

(10) Patent No.: US 6,464,495 B1
(45) Date of Patent: Oct. 15, 2002

(54) GNATHOLOGICAL BITE OPENER

(75) Inventor: John C. Voudouris, Toronto (CA)

(73) Assignee: OrthoArm, Inc. (CA)

( * ) Notice: Subject to any disclaimer, the term of this patent is extended or adjusted under 35 U.S.C. 154(b) by 0 days.

(21) Appl. No.: 09/651,013

(22) Filed: Aug. 29, 2000

(51) Int. Cl.$^7$ ................................................ A61C 7/00
(52) U.S. Cl. ........................................ 433/18; 433/19
(58) Field of Search ............................ 433/18, 6, 24, 433/19, 215; 128/857, 861, 862, 859

(56) References Cited

U.S. PATENT DOCUMENTS

| | | | | |
|---|---|---|---|---|
| 3,787,976 A | * | 1/1974 | Cohen | 433/3 |
| 4,419,992 A | | 12/1983 | Chorbajian | 128/136 |
| 4,445,861 A | * | 5/1984 | Klepacki | 433/181 |
| 4,609,350 A | * | 9/1986 | Krause | 433/7 |
| 4,799,500 A | | 1/1989 | Newbury | 128/859 |
| 5,110,290 A | * | 5/1992 | Wong | 433/9 |
| 5,566,683 A | | 10/1996 | Thornton | 128/848 |
| 5,957,686 A | | 9/1999 | Anthony | 433/19 |
| 5,964,587 A | * | 10/1999 | Sato | 433/6 |

OTHER PUBLICATIONS

Intraoral/Noncompliance, Section 9, p. 3; "Bite Turbos"; *Ormco Product Catalog*; p. 158.

* cited by examiner

Primary Examiner—Nicholas D. Lucchesi
Assistant Examiner—Melba Bumgarner
(74) Attorney, Agent, or Firm—Michael Best & Friedrich LLP

(57) ABSTRACT

The invention is directed to orthodontic devices that provide anterior guidance to teeth situated opposite thereto so as to inhibit excessive or uncontrollable grinding and clenching of teeth. The claimed invention is also directed to methods of opening the bite with anterior guidance.

10 Claims, 3 Drawing Sheets

GNATHOLOGICAL BITE OPENER

FIELD OF THE INVENTION

The present invention relates to gnathological bite openers. More particularly, the present invention relates to gnathological bite openers adapted to provide anterior guidance to the opposing teeth in order to inhibit grinding and clenching of teeth.

BACKGROUND OF THE INVENTION

Many individuals grind and clench their teeth inadvertently, especially at night. Tooth grinding and clenching causes significant problems including wearing of tooth enamel and cosmetic damage. Grinding and clenching of teeth also exacerbates problems associated with the temporomandibular joint and the surrounding muscles, often referred to as temporomandibular disorder.

In order to prevent tooth grinding and clenching and alternatively to assist people in ceasing this behavior, orthodontists have developed devices termed as "bite openers". Examples of conventional bite openers include mouthpieces which cover or surround multiple teeth of the upper and/or lower jaw. The conventional bite openers are bulky and uncomfortable to wear. Many such devices render eating and speaking difficult if not impossible; hence they can only be worn at night. Finally, such devices are generally expensive and complicated to manufacture.

Other bite openers are less bulky but have other disadvantages that make them uncomfortable and impractical. For example, bite openers have been devised to bond to the lingual surface of one or more front teeth. One such devise includes a shelf-like flat plane which protrudes perpendicularly or at an angle (e.g., 45°) from the lingual surface of the tooth to which it is attached. Patients find bite openers uncomfortable as the flat plane protrudes toward the tongue causing discomfort to the tongue and difficulty in speaking. In addition, such devices commonly include corners and sharp edges which can cause discomfort to the walls of the mouth and to the tongue. Further, although such devices prevent grinding, the upper tips of the mandibular front teeth grind upwardly against the device itself. Since these devices are typically made of a hard substance, the cusps of the opposing teeth are highly susceptible to enamel damage. The labial surfaces of the mandibular teeth are also damaged by forceful collision or grinding against the flat plane of the device. Finally, the mandibular front teeth often slide along the plane of the bite opener (toward the mouth cavity) grinding against, and placing undue force on the maxillary front teeth bearing the device.

Still another shortcoming of bite openers such as mouthpieces and smaller devices that include corners and ledges is that the straight planes of these devices disrupt the normal gnathological relationship between the mandibular and maxillary teeth. Specifically, the lingual surfaces of normal human anterior maxillary teeth are shaped like an "S" or a saddle, providing a gradual slope from the gingiva to the tips of the teeth. When the anterior mandibular teeth push or grind in a forward direction against the anterior maxillary teeth, the tips of the mandibular teeth engage the sloped lingual surface of the maxillary teeth. The forward force against this slope causes the mandibular teeth to slide gently along the lingual side of the maxillary teeth in a downwardly forward direction and to lift off of the front teeth. Thus, the mandibular teeth are caused to slide off of the maxillary teeth, and the teeth do not collide. This movement is called "anterior guidance" or "anterior lift off." The conventional bite openers not only fail to provide anterior guidance, but they also prevent the lingual surfaces of the anterior maxillary teeth from providing anterior guidance.

SUMMARY OF THE INVENTION

The claimed invention is directed to orthodontic devices that provide anterior guidance to teeth situated opposing thereto. The claimed invention is also directed to methods of opening the bite while providing anterior guidance.

BRIEF DESCRIPTION OF THE DRAWINGS

The various features of the invention will best be appreciated by simultaneous reference to the description which follows and the accompanying drawings, in which.

DETAILED DESCRIPTION

Figure 1:
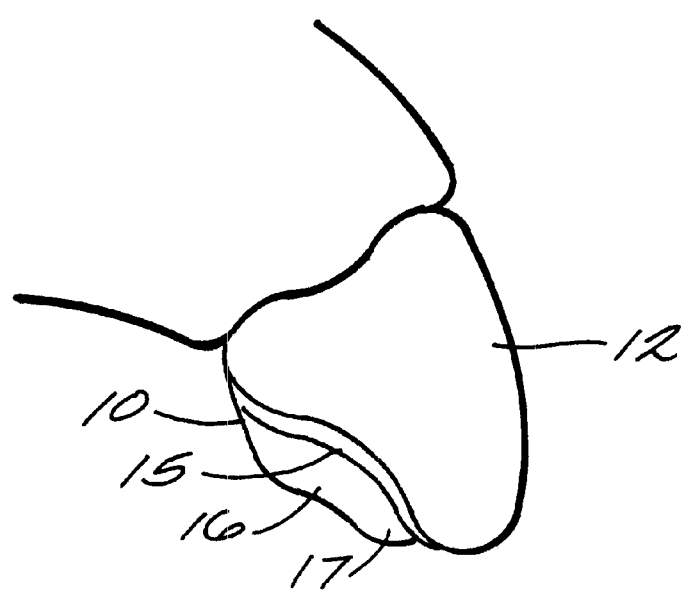
FIG. 1 is a side view of one embodiment of a gnathological bite opener according to the present invention as mounted on a tooth.

FIG. 1 is a side view of an embodiment of a gnathological bite opener 10 according to the present invention as mounted on a tooth 12. As schematically presented in FIG. 1, device 10 of the present invention comprises two surfaces that are approximately parallel to one another. A first surface or the mounting surface 15 is adapted for mounting on a lingual surface of at least one anterior tooth of the patient. In one embodiment, the shape of mounting surface 15 can be substantially convex, such that the curve of the mounting surface approximates or mirrors the curvature of the lingual surface of anterior tooth 12. In another embodiment, anterior tooth 12 can be a maxillary tooth. In yet another embodiment, the anterior maxillary tooth can be an incisor. In all of the above embodiments the shape of the tooth can be a design factor in deciding the curvature of mounting surface 12. Alternatively, mounting surface 12 can have a flat, concave or convex shape.

The second surface or the guiding surface 16 can be defined in a number of shapes depending on the patient's particular needs. Among the alternative embodiments of the present invention guiding surface 16 can have (i) a substantially flat surface, (ii) a substantially concave or convex surface in a plane parallel to the lingual surface of tooth 12 when mounting surface 15 is in contact with tooth 12, (iii) can have a an "S-shaped" surface, (iv) can have a saddle-shaped surface or (v) can be shaped substantially similar to lingual surface of the tooth to which it is attached. In another embodiment of the invention guiding surface 15 is shaped such that the forces exerted thereon by the opposing tooth are redirected back enabling the bite to open. By way of example, FIGS. 1–4 schematically represent saddle-shaped curve according to one embodiment of the invention.

The mounting surface 15 and guiding surface 16 are separated by a thickness 17, as schematically shown in FIGS. 1–4. Thickness 17 is adapted to provide a bite-opening effect when the device is attached to the lingual side of the tooth. In other words, thickness 17 is adapted to redirect the force so as to cause a bite opening. Of course, the thickness could vary depending on the patient's over-bite or under-bite. Thickness 17 can also be uniform at the center of the bite opener while gradually tapering toward the edges, as schematically represented in FIGS. 1–4.

Figure 3:
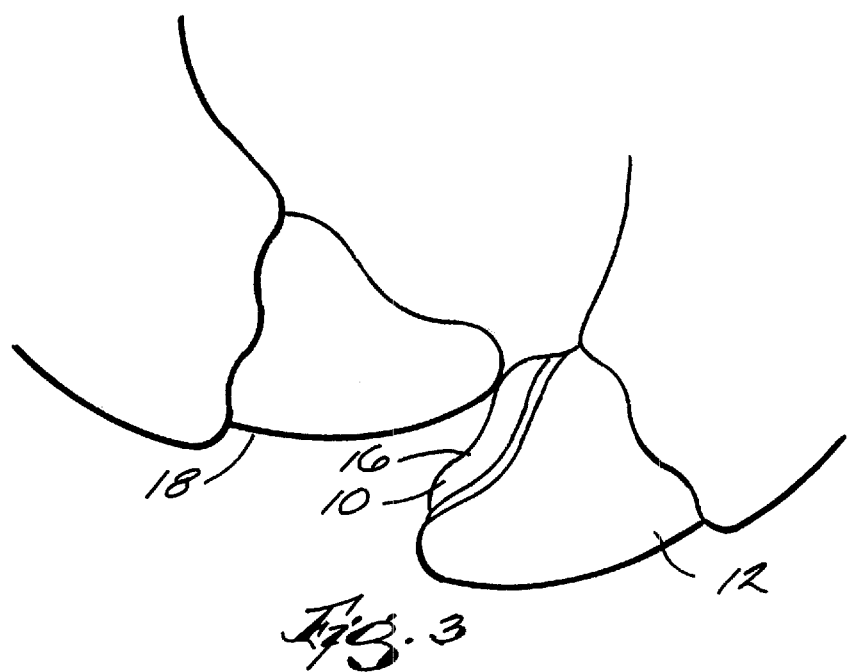
FIG. 3 is a side view of an embodiment of a gnathological bite opener according to the present invention mounted on a tooth and engaging an opposing tooth.

FIG. 3 is a side view of an embodiment of a bite opener of the present invention mounted on tooth 12 and engaging an opposing tooth 18. As schematically illustrated, guiding surface 16 is adapted such that the bite opener engages at least one opposing tooth 18. This composition enables the bite opener to push opposing tooth 18 away.

Figure 4:
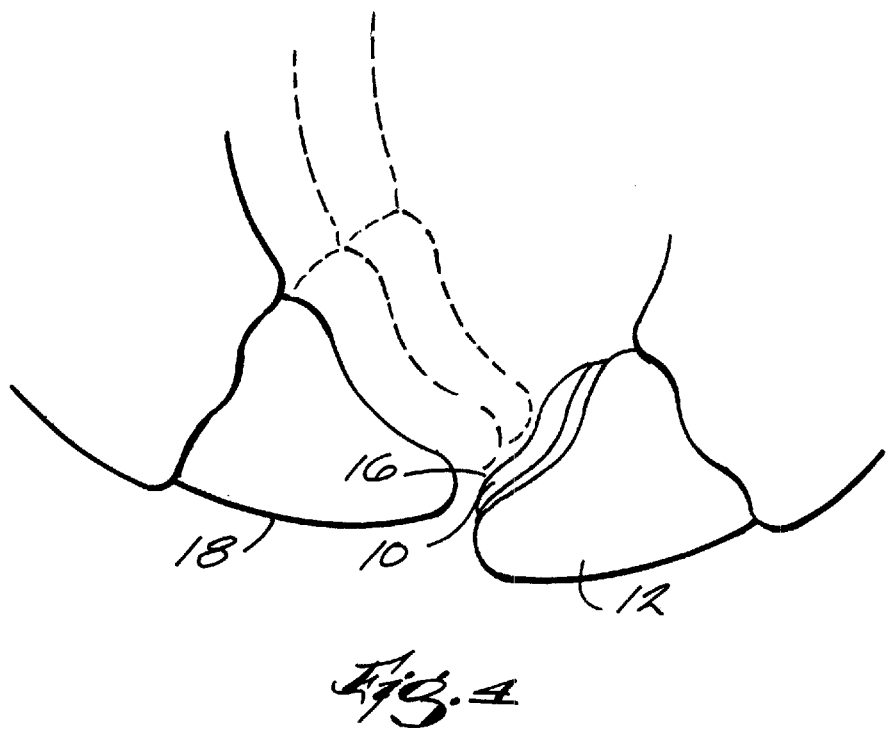
FIG. 4 is a side view of an embodiment of a gnathological bite opener according to the present invention mounted on a tooth and providing anterior guidance to an opposing tooth.

FIG. 4 is a side view of a bite opener according to an embodiment of the present invention as mounted on tooth 12 and providing anterior guidance to opposing tooth 18. As stated, guiding surface 16 can be adapted to provide anterior guidance to an opposing tooth 18. Tooth 18 can be a mandibular tooth or an incisor. When tooth 18 engages the bite opener with an upward or forward-direction force, the bite opener redirects the force in a downward direction such that opposing tooth 18 slides downwardly and away from guiding surface 16. For example, when the bite opener is mounted on the maxillary teeth, the mandibular teeth opposite thereto will engage the bite opener during grinding or clenching, but will release as the bite opener redirects the force in the opposing direction. Conversely, where the bite opener is attached to the mandibular teeth (for example in patients suffering from under-bite), the maxillary teeth opposing the bite opener would be directed away from the bite opener as they exert grinding or clenching force thereto.

Figure 2:
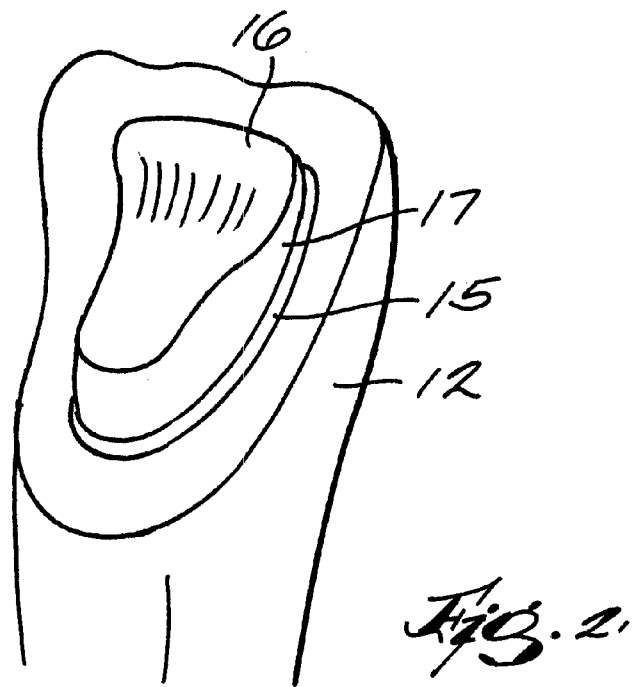
FIG. 2 is a perspective view of a gnathological bite opener according to the an embodiment of the present invention as mounted on a tooth.

FIG. 2 illustrates a perspective view of a gnathological bite openers 10 according to the present invention mounted on a tooth. A bite opener can be centered in the middle of a tooth. A bite opener can cover from 50% to 75% of the lingual surface of a tooth. In another embodiment, a bite opener can cover from 25% to 100% of the lingual surface of a tooth. Of course, each of the placement and the tooth coverage of bite openers according to the present invention may vary according to patients' conditions.

As stated, a bite opener can be strategically attached to the lingual surface of more than one type of tooth. For example, the bite opener can be attached to adjacent teeth such as the maxillary central incisors, the central mandibular incisors or the lateral incisors. In another embodiment, one bite opener can be attached to the lingual surfaces of two or more teeth. In these embodiments, the device of the present invention can be constructed wide enough to span the lingual surfaces of the teeth to be covered.

The material of construction for the bite opener of the present invention can be selected from among the conventional material including biologically suitable composites and alloys. For examples, the bite opener of the present invention can be made of a material having adequate balance of hardness (to prevent deformation through grinding) and non-brittleness (to prevent shattering or cracking). Suitable material of construction include, for example: ceramics, plastics, ceramic reinforced plastics, composites, resins, acrylics, stainless steel, cobalt-chromium alloys, gold, titanium and other metals or alloys thereof. The bite opener of the present invention can be constructed through conventional techniques such as metal injection molding, molding, milling, injection molding, casting and machining. Other suitable methods which enable customization of the bite opener to the patient's specific needs as well as large-scale production of standard-size bite openers are considered within the scope of the present invention.

The bite opener of the present invention is preferably attached to the tooth by any of the conventionally known methods for temporary, permanent and semi-permanent bonding. For example, the bite opener can be attached by applying, either alone or in combination, mechanical fastening or chemical bonding. Other examples include chemical curable bonding, light curable bonding, bonding resin alone, or in combination with a bonding mesh such as SUPERMESH® or metal mesh available from GAC International, Inc. As yet another example, a stainless steel bonding pad may be used alone or in combination with a bonding mesh, such as SUPERMESH®, or a bonding resin.

In certain embodiments, bonding devices are brazed together. As examples, a bite opener may be brazed to SUPERMESH® or to a stainless steel bonding pad, or SUPERMESH® may be brazed to a stainless steel bonding pad. In one such embodiment, a stainless steel bite opener is brazed to a stainless steel bonding pad, which is bonded to SUPERMESH®. Such an assembly, i.e., bite opener-bonding pad SUPERMESH®, may be attached to a tooth by bonding the SUPERMESH® to the tooth by any suitable bonding or fastening method.

The length of treatment with bite openers according to the present invention may vary according to patients' conditions and progress. Bite opening devices according to the present invention may be removed from teeth using any suitable method. Suitable methods include those used to remove brackets from teeth. As an example, bite openers of the present invention may be removed using debonding pliers or hard wire cutters.

Figure 5:
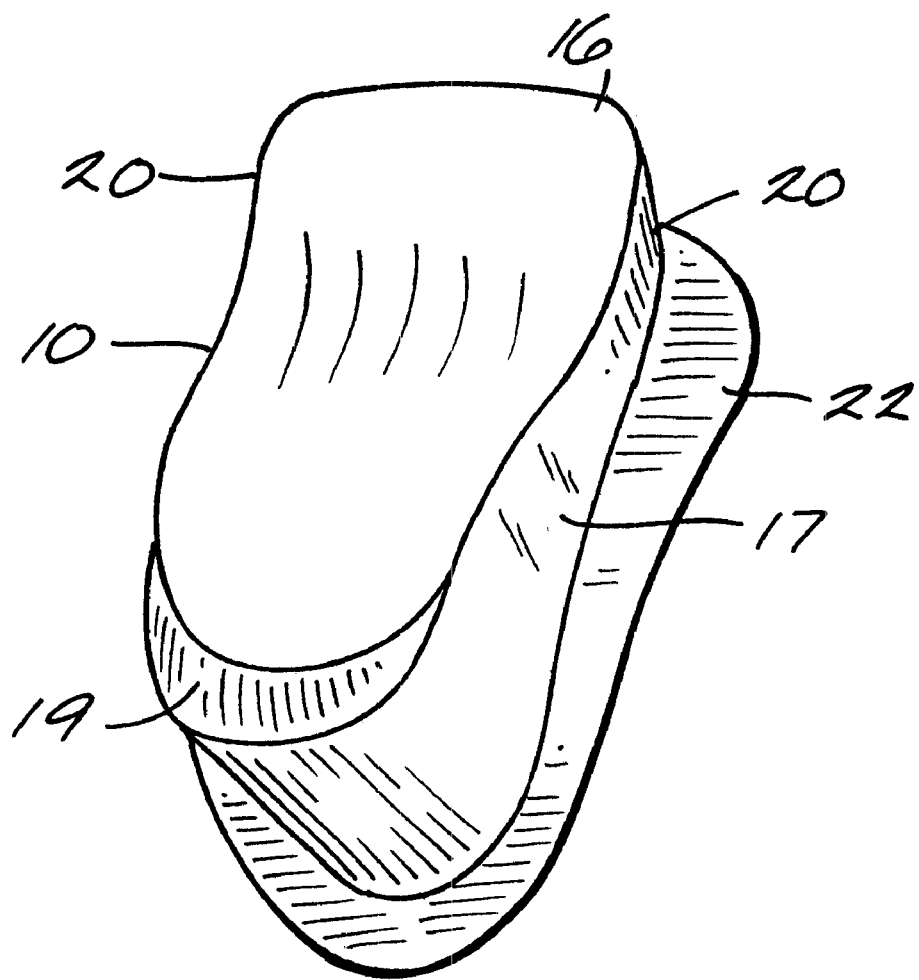
FIG. 5 is a schematic representation of a gnathological bite opener with sides adapted for ease of handling and installation.

FIG. 5 is a schematic representation of a gnathological bite opener with sides adapted for ease of handling and installation. In the preferred embodiment of FIG. 5, thickness 17 of bite opener 10 is concaved to enable ease of handling. While FIG. 5 shows the thickness as being concave, other distinguishing surfaces can be formed on thickness 17 to accomplish the same task and are considered within the scope of the present invention. For example, in another embodiment, surface 10 can be serrated or include a plurality of indentations which enable securing by an instrument. As such, the indentations or the concavity can be adapted to couple the tips of orthodontic pliers or tweezers. In addition, as schematically illustrated in FIG. 5, surface 19 is beveled with respect to guiding surface 16 and sides 20, are substantially parallel to each other. Finally, in FIG. 5, bonding pad 22 adheres bite opener 10 to the tooth.

In one embodiment, a bite opener includes a cavity. Such a cavity facilitates the crushing or collapsing of the bite opener, thereby aiding in its removal. The cavity, for example, can be hollow or filled with a material softer than the material forming the bite opener. Alternatively, the cavity can be sealed such that the cavity is not exposed to the mouth when the bite opener is attached to a tooth. In yet another alternative embodiment, the cavity can be a channel, extending for example, in the longitudinal axis of the bite opener. Bonding adhesive, bonding mesh, or other material remaining on the tooth after removal of bite openers according to the present invention may be removed using a scraping device, such as a debonding scaler.

While description presented herein is directed to prevention of tooth damage from excessive grinding, it is noted that the bite openers of the present invention are useful in treating sleep apnea as they maintain the breathing passage open. In addition, the bite openers can assist other orthodontic treatments by opening the bite thereby preventing the tips of the maxillary teeth from scraping against orthodontic braces assembled on the mandibular teeth. More importantly, the bite openers of the present invention are particularly useful to patients suffering from temporomandibular disorder. By inhibiting grinding and clenching of teeth, bite openers of the present invention can prevent further damage to the temporomandibular joint and associated muscles, reduce discomfort from already-existing damage and allow healing. Accordingly, it will be noted that the bite opener of the present invention is not limited to applications relating to bite adjustment.

What is claimed is:

1. A bite opening device comprising:

a body having a mounting surface and a guiding surface, the guiding surface substantially separated from the mounting surface by a thickness, wherein the mounting surface is defined by a substantially convex contour adapted to be mounted on a lingual surface of at least a first anterior tooth, and wherein the guiding surface is capable of providing anterior guidance to at least a second anterior tooth, and wherein the guiding surface is defined by a substantially concave contour in a plane parallel to the lingual surface of the first anterior tooth.

2. The bite opening device of claim 1, wherein the guiding surface is capable of engaging at least a second anterior tooth.

3. The bite opening device of claim 1, wherein the guiding surface comprises a saddle-shaped curve in the plane parallel to the lingual surface of the first anterior tooth.

4. The bite opener of claim 1 wherein said thickness is adapted to facilitate handling.

5. A method for opening the bite of a subject comprising:

providing a device comprising a mounting surface and a guiding surface, the mounting surface adapted to be positioned substantially adjacent to a first anterior tooth, the guiding surface being defined by a substantially concave contour in a plane parallel to the lingual surface of the first anterior tooth and capable of providing anterior guidance to a second anterior tooth; and positioning the mounting surface adjacent to a lingual side of at least one anterior tooth.

6. The method of claim 5, wherein said positioning is accomplished by using mechanical fasteners.

7. The method of claim 5, wherein said positioning is accomplished by using adhesives.

8. A kit comprising:

a bite opening device comprising a body having a mounting surface adapted to be mounted on a lingual surface of at least a first anterior tooth and a guiding surface capable of providing anterior guidance to at least a second anterior tooth, said guiding surface being defined by a substantially concave contour in a plan substantially parallel to said mounting surface and a bonding pad.

9. The kit of claim 8, wherein:

the mounting surface substantially forms a convex contour adapted to be mounted on the lingual surface of at least one anterior maxillary tooth, the guiding surface capable of providing anterior guidance to at least one anterior mandibular tooth.

10. The kit of claim 8, wherein:

said bonding pad comprises metal mesh.

* * * * *

UNITED STATES PATENT AND TRADEMARK OFFICE
CERTIFICATE OF CORRECTION

PATENT NO.     : 6,464,495 B1
DATED          : October 15, 2002
INVENTOR(S)    : John C. Voudouris It is certified that error appears in the above-identified patent and that said Letters Patent is hereby corrected as shown below:

Column 6,
Line 21, "plan" should be -- plane --.

Signed and Sealed this

Sixth Day of January, 2004

JAMES E. ROGAN
*Director of the United States Patent and Trademark Office*